(12) United States Patent
Jensen et al.

(10) Patent No.: US 8,187,200 B2
(45) Date of Patent: May 29, 2012

(54) METHOD AND APPARATUS TO DETECT AND MONITOR THE FREQUENCY OF OBSTRUCTIVE SLEEP APNEA

(75) Inventors: Donald N. Jensen, Derwood, MD (US); Catherine R. Condie, Shoreview, MN (US); Yong Kyun Cho, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 234 days.

(21) Appl. No.: 12/369,899

(22) Filed: Feb. 12, 2009

(65) Prior Publication Data

US 2009/0209880 A1 Aug. 20, 2009

Related U.S. Application Data

(60) Division of application No. 11/284,283, filed on Nov. 21, 2005, now Pat. No. 7,509,164, which is a continuation of application No. 10/136,778, filed on Apr. 30, 2002, now abandoned.

(51) Int. Cl.
*A61B 5/085* (2006.01)
(52) U.S. Cl. .......................... 600/534; 607/17
(58) Field of Classification Search .................. 600/529, 600/532–534, 536, 547; 607/17
See application file for complete search history.

(56) References Cited

U.S. PATENT DOCUMENTS

| | | |
|---|---|---|
| 4,422,458 A | 12/1983 | Kravath |
| 4,803,997 A | 2/1989 | Bowman |
| 5,016,636 A | 5/1991 | Kulakowski |
| 5,133,345 A | 7/1992 | Lambert |
| 5,957,861 A | 9/1999 | Combs et al. |
| 6,449,509 B1* | 9/2002 | Park et al. .......... 607/20 |
| 6,491,647 B1* | 12/2002 | Bridger et al. .......... 600/585 |
| 6,741,885 B1* | 5/2004 | Park et al. .......... 600/509 |
| 6,928,324 B2* | 8/2005 | Park et al. .......... 607/20 |
| 2001/0037067 A1* | 11/2001 | Tchou et al. .......... 600/483 |

OTHER PUBLICATIONS

Bahammam, A. et al., "Decision Making in Obstructive Sleep-Disordered Breathing: Putting It All Together," Clin Chest Med, vol. 19, p. 87-97 (1998).
Deegan, P.C. et al., "Pathophysiology of Obstructive Sleep Apnea," Eur Resp J, vol. 8, p. 1161-78 (1995).
Findley, L. et al., "Automobile Accidents Involving Patients with Obstructive Sleep Apnea," Am Rev Respir Dis, vol. 138, p. 337-340 (1988).
Fletcher, E.C. et al., "Undiagnosed Sleep Apnea in Patients With Essential Hypertension," Ann Intern Med, vol. 103, p. 190-4 (1985).
Gonzalez-Rothi, R. et al., "Do Patients with Sleep Apnea Die in Their Sleep?," Chest, vol. 94, p. 531-8 (1988).

(Continued)

*Primary Examiner* — Kennedy Schaetzle
*Assistant Examiner* — Erica Lee
(74) *Attorney, Agent, or Firm* — Scott A. Bardell; Stephen W. Bauer; Evans M. Mburu

(57) ABSTRACT

The present invention provides a method and apparatus for detecting and monitoring obstructive sleep apnea. The apparatus includes an intracardiac impedance sensor to measure intracardiac impedance, a movement sensor to measure an amount of movement of a patient, and a controller operatively coupled to said intracardiac impedance sensor and said movement sensor, said controller adapted to receive at least one of an intracardiac impedance and the amount of movement of the patient and detect obstructive sleep apnea based upon said intracardiac impedance and said movement.

9 Claims, 4 Drawing Sheets

OTHER PUBLICATIONS

Grimm, W. et al., "Symptoms, Cardiovascular Risk Profile and Spontaneous ECG in Paced Patients: a Five-Year Follow-Up Study," PACE, vol. 13, p. 2086-90 (1990).

Guilleminault, C. et al., "Cardiac Arrhythmia and Conduction Disturbances During Sleep in 400 Patients with Sleep Apnea Syndrome," Am J Cardiol, vol. 52, p. 490-4 (1983).

He, J. et al., "Mortality and Apnea Index in Obstructive Sleep Apnea Patients: Experience in 385 Male Patients," Chest, vol. 94, p. 9-14 (1988).

Javaheri, S. et al., "Occult Sleep-Disordered Breathing in Stable Congestive Heart Failure," Ann intern Med, vol. 122, p. 487-92 (1995).

Jenkinson, C. et al., "Comparison of Therapeutic and Subtherapeutic Nasal Continuous Positive Airway Pressure for Obstructive Sleep Apnoea: a Randomized Prospective Parallel Trial," Lancet, vol. 353, p. 2100-85 (1999).

Kales, A et al., "Sleep Apnea in a Hypertensive Population," Lancet, vol. 2, p. 1005-8 (1984).

Krieger, J. et al., "Left Ventricular Ejection Fraction in Obstructive Sleep Apnea: Effect of Long Term Treatment with Nasal Continuous Positive Airway Pressure," Chest, vol. 100, p. 917-21 (1991).

Kryger, M.H. et al., "Utilization of Health Care Services in Patients with Severe Obstructive Sleep Apnea," Sleep, vol. 19, p. S111-6 (1996).

Lavie, P. et al., "Prevalence of Sleep Apnea Among Patients with Essential Hypertension," *Am. Heart J.,* vol. 108, p. 373-6 (1984).

Lichstein, K.L. et al., "Occult Sleep Apnea in a Recruited Sample of Older Adults with Insomnia," J Consult Clin Psych, vol. 67, p. 405-10 (1999).

Malone, S. et al., "Obstructive Sleep Apnea in Patients with Dilated Cardiomyopathy: Effects of Continuous Positive Airway Pressure," Lancet, vol. 338, p. 1480-4 (1991).

Man, G.C.W., "Obstructive Sleep Apnea, Diagnosis and Treatment," Med Clin North Am, vol. 80, p. 803-20 (1996).

Millman, R.P. et al., "Daytime Hypertension in Obstructive Sleep Apnea, Prevalence and Contributing Risk Factors," Chest, vol. 99, p. 861-66 (1991).

Naughton, M.T. et al., "Sleep Apnea in Congestive Heart Failure," Clin Chest Med, vol. 19, p. 99-113 (1996).

Naughton, M.T. et al., "Pathophysiology and Treatment of Cheyne-Stokes Respiration," Thorax, vol. 53, p. 514-18 (1998).

Palomaki, H., "Snoring and the Risk of Ischemic Brain Infarction," Stroke, vol. 22, p. 1021-25 (1991).

Partinen, M. et al., "Long-Term Outcome for Obstructive Sleep Apnea Syndrome Patients: Mortality," Chest, vol. 94, p. 1200-4 (1988).

Partinen, M. et al., "Daytime Sleepiness and Vascular Mortality at Seven-Year Follow-Up in Obstructive Sleep Apnea Patients," Chest, vol. 97, p. 27-32 (1990).

Peter, J.H. et al., "Manifestations and Consequences of Obstructive Sleep Apnoea," Eur Respir J, vol. 8, p. 1572-83 (1995).

Ronald, J. et al., "Health Care Utilization in the 10 Years Prior to Diagnosis in Obstructive Sleep Apnea Syndrome Patients," Sleep, vol. 22, p. 225-9 (1999).

Shepard, J.W., "Hypertension, Cardiac Arrhythmias, Myocardial Infarction, and Stroke in Relation to Obstructive Sleep Apnea," Clinics in Chest Med, vol. 13, p. 437-58 (1992).

Skomro, R.P. et al., "Clinical Presentations of Obstructive Sleep Apnea Syndrome," Progress Cardiovasc Dis, vol. 41, p. 331-340 (1999).

Strohl, K.P. et al., "Sleep Apnea, Sleepiness, and Driving Risk: Official Statement of the American Thoracic Society," Am J Resp Crit Care Med, vol. 150, p. 1463-73 (1994).

Strollo, Jr., P.J. et al., "Current Concepts: Obstructive Sleep Apnea," N Engl J Med, vol. 334, p. 99-104 (1996).

Tilkian, A.G. et al., "Sleep-Induced Apnea Syndrome: Prevalence of Cardiac Arrhythmias and Their Reversal After Tracheostomy," Am J Med, vol. 63, p. 348-58 (1977).

Weiss, J.W. et al., "Cardiovascular Morbidity in Obstructive Sleep Apnea," Prog Cardiovasc Dis, vol. 41, p. 367-76 (1999).

Wietzenblum, E. et al., "Daytime Pulmonary Hypertension in Patients with Obstructive Sleep Apnea Syndrome," Am Rev Resp Dis, vol. 138, p. 345-9 (1988).

Williams, A.J. et al., "Sleep Apnea Syndrome and Essential Hypertension," Am J Cardiol, vol. 55, p. 1019-22 (1985).

Yamashiro, Y. et al., "Why Should Sleep Apnea Be Diagnosed and Treated?" Clin Pulm Med, vol. 1, p. 250-9 (1994).

Young, T. et al., "Estimation of the Clinically Diagnosed Proportion of Sleep Apnea Syndrome in Middle-Aged Men and Women," *Sleep*, vol. 20, p. 705-6 (1999).

Zwillich, C. et al., "Bradycardia During Sleep Apnea: Characteristics and Mechanisms," J Clin Invest, vol. 69, p. 1286-92 (1982).

* cited by examiner

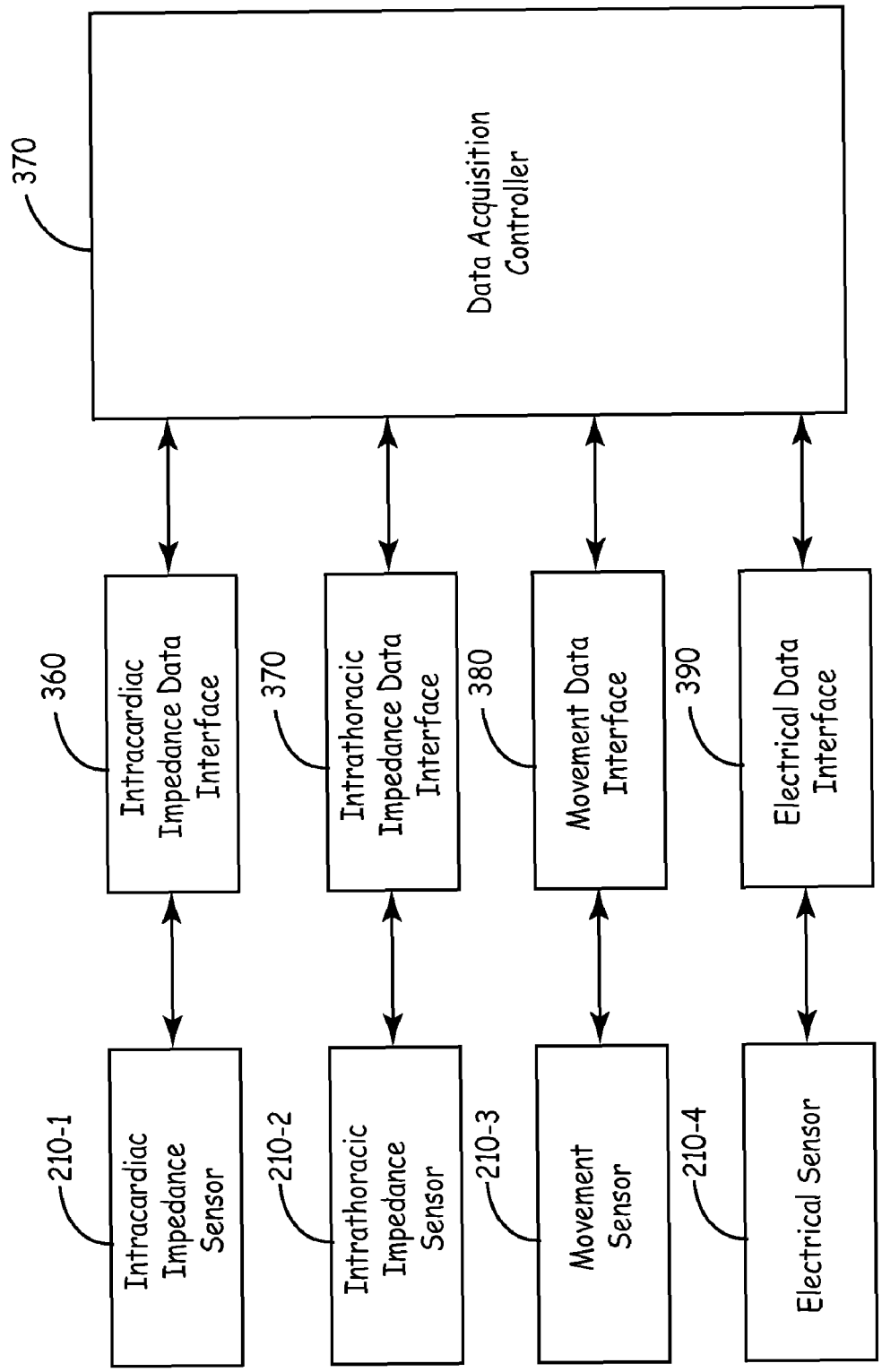

METHOD AND APPARATUS TO DETECT AND MONITOR THE FREQUENCY OF OBSTRUCTIVE SLEEP APNEA

BACKGROUND OF THE INVENTION

This application is divisional of application Ser. No. 11/284,283, filed on Nov. 21, 2005 which is a continuation of application Ser. No. 10/136,778, filed Apr. 30, 2002.

FIELD OF THE INVENTION

This invention relates generally to implantable medical devices, and more particularly, to a method and apparatus to automatically detect and monitor the frequency of obstructive sleep apnea.

DESCRIPTION OF THE RELATED ART

Although the function of sleep is not well understood, one consequence of an inadequate quantity or poor quality of sleep is an inability to maintain adequate wakefulness. The amount of sleep an individual needs is thought to be neurologically determined and is generally stable over time. Among other factors, an insufficient amount of sleep (i.e., quantity of sleep) or a disruption of sleep continuity (i.e., quality of sleep) will result in increased daytime sleepiness. Increased sleepiness in a person may cause a plethora of problems to that person as well as others. Increased sleepiness is a major cause of accidents because people who are sleepy are generally not fully aware of their surroundings. Additionally, because of this decreased awareness, a person who does not receive the adequate quantity and quality of sleep at night may also be prone to decreased efficiency at home and at work. A sleepy person may also require frequent naps during the day to recuperate, thereby reducing productivity in the office as well as in the chores of daily life. As a result, it is important for people generally to receive a good night's rest. However, many people have medical conditions that prevent them from receiving a good night's rest. One such condition is sleep apnea.

Sleep apnea is generally defined as the cessation of breathing during sleep. One type of a sleep apnea, obstructive sleep apnea ("OSA"), is caused by repetitive upper airway obstruction during sleep as a result of narrowing of the respiratory passages. Partial obstruction of the passageways may simply lead to hypopnea. Prolonged obstruction of the passageways, however, may lead to nocturnal arousals.

OSA is generally characterized by a sleep-related withdrawal of upper airway inspiratory muscle tone superimposed on a narrow, highly compliant pharynx. As a result, the pharynx may during sleep, leading to obstructive apnea.

The cause of OSA is thought to be a combination of anatomic characteristics of the upper airway and abnormalities in the neuromuscular control of the muscles in the throat. Sleep apnea is more common in individuals with large tonsils, palate, and tongue, and with a short thick neck. This anatomy may predispose the throat to easily collapse. A badly deviated nasal septum or other nasal obstruction can also worsen OSA because it limits the ability to breathe through the nose. Overweight individuals are also at high risk for OSA. Not all individuals with these anatomic features will have OSA, and OSA occasionally occurs in people with normal-appearing throats.

OSA may cause a variety of medical and other problems among patients. Cycles of sleep, snoring, obstruction, arousal, and sleep may occur many times throughout the night. Although such nocturnal arousals may last only a few seconds, they prevent a person from reaching the deep stages of sleep, which the body generally needs to rest and replenish its strength. As a result, patients with OSA may not receive a restful sleep because of multiple nocturnal arousals.

Furthermore, multiple arousals with sleep fragmentation are likely to cause excessive daytime sleepiness and fatigue, cognitive impairment, depression, headaches, chest pain, and diminished sexual drive. OSA is generally associated with cardiovascular morbidity, including systemic hypertension, pulmonary hypertension, ischemic heart disease, stroke, and cardiac arrhythmias. OSA is also usually associated with increased mortality by negatively affecting the status, progression, and outcomes of previously existing conditions, such as congestive heart failure ("CHF").

OSA is a disorder which is generally underdiagnosed and undertreated. Because OSA may worsen the effects of a previously existing condition, such as CHF, treatment of OSA may be beneficial to reduce its negative on the previously existing condition. Once OSA has been properly diagnosed, a variety of therapies may be available. Common OSA therapies include non-surgical methods, such as continuous positive airway pressure ("CPAP"), as well as surgical methods, such as uvulopalatopharyngoplasty ("UPPP"). Effective therapy for OSA can often reverse or ameliorate the problems associated with OSA.

One method of diagnosis for OSA is nocturnal polysomnography. In nocturnal polysomnography, multiple physiological parameters are measured while the patient sleeps in a laboratory. Typical parameters in a nocturnal polysomnography include eye movement observations (to determine whether a patient has reached REM sleep), an electroencephalogram (to determine arousals from sleep), chest wall monitors (to document respiratory movements), nasal and oral air-flow measurements, and an electrocardiogram, among other parameters. A combination of these and other factors are used by doctors and other qualified sleep specialists to determine whether a patient has OSA. However, nocturnal polysomnography is generally expensive and time-consuming. Furthermore, many patients experience the symptoms of OSA (e.g., nocturnal arousals, snoring) while they are asleep, and therefore, never recognize that they may have a sleeping disorder. As a result, many patients with OSA may not seek proper diagnosis or treatment of their sleeping disorder from a doctor or other qualified sleep specialist. Even if a patient is diagnosed with OSA, frequent laboratory monitoring of the patient is generally not feasible due to the expense and time involved in a nocturnal polysomnography.

The technology explosion in the implantable medical devices industry has resulted in many new and innovative devices and methods for analyzing and improving the health of a patient. The class of implantable medical devices now includes pacemakers, implantable cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

There are many implementations of implantable medical devices that provide data acquisition of important physiological data from a human body. Many implantable medical devices are used for cardiac monitoring and therapy. Often these devices comprise sensors that are placed in blood vessels and/or chambers of the heart. Often these devices are operatively coupled with implantable monitors and therapy delivery devices. For example, such cardiac systems include implantable heart monitors and therapy delivery devices, such as pacemakers, cardioverters, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram ("EGM").

Many patients who use implantable medical devices may be at risk for OSA. However, patients are generally left with traditional forms of diagnosis for OSA, such as nocturnal polysomnography. As mentioned, nocturnal polysomnography may be an expensive and time-consuming procedure. Furthermore, many patients may not recognize that they have symptoms relating to OSA, such that they would seek diagnosis and treatment for the disorder. Nocturnal polysomnography is generally an infrequent procedure that does not provide long term monitoring of the patient's condition after he has been diagnosed. The present invention is directed to overcoming, or at least reducing the effects of, one or more of the problems set forth above.

SUMMARY OF THE INVENTION

In one aspect of the present invention, an apparatus is provided for detecting and monitoring obstructive sleep apnea. The apparatus includes an intracardiac impedance sensor to measure intracardiac impedance, a movement sensor to measure an amount of movement of a patient, and a controller operatively coupled to said intracardiac impedance sensor and said movement sensor, said controller adapted to receive at least one of an intracardiac impedance and the amount of movement of the patient and detect obstructive sleep apnea based upon said intracardiac impedance and said movement.

In another aspect of the present invention, a method is provided for detecting and monitoring obstructive sleep apnea. The method includes measuring an intracardiac impedance to detect a change in the intracardiac impedance, measuring an amount of movement of a patient, and determining the presence of obstructive sleep apnea based upon the change in the intracardiac impedance and the movement of the patient.

BRIEF DESCRIPTION OF THE DRAWINGS

The invention may be understood by reference to the following description taken in conjunction with the accompanying drawings, in which like reference numerals identify like elements, and in which:

FIG. 4 illustrates a more detailed block diagram representation of a plurality of sensors and its associated data interfaces of FIG. 3, in accordance with one illustrative embodiment of the present invention.

Figure 1:
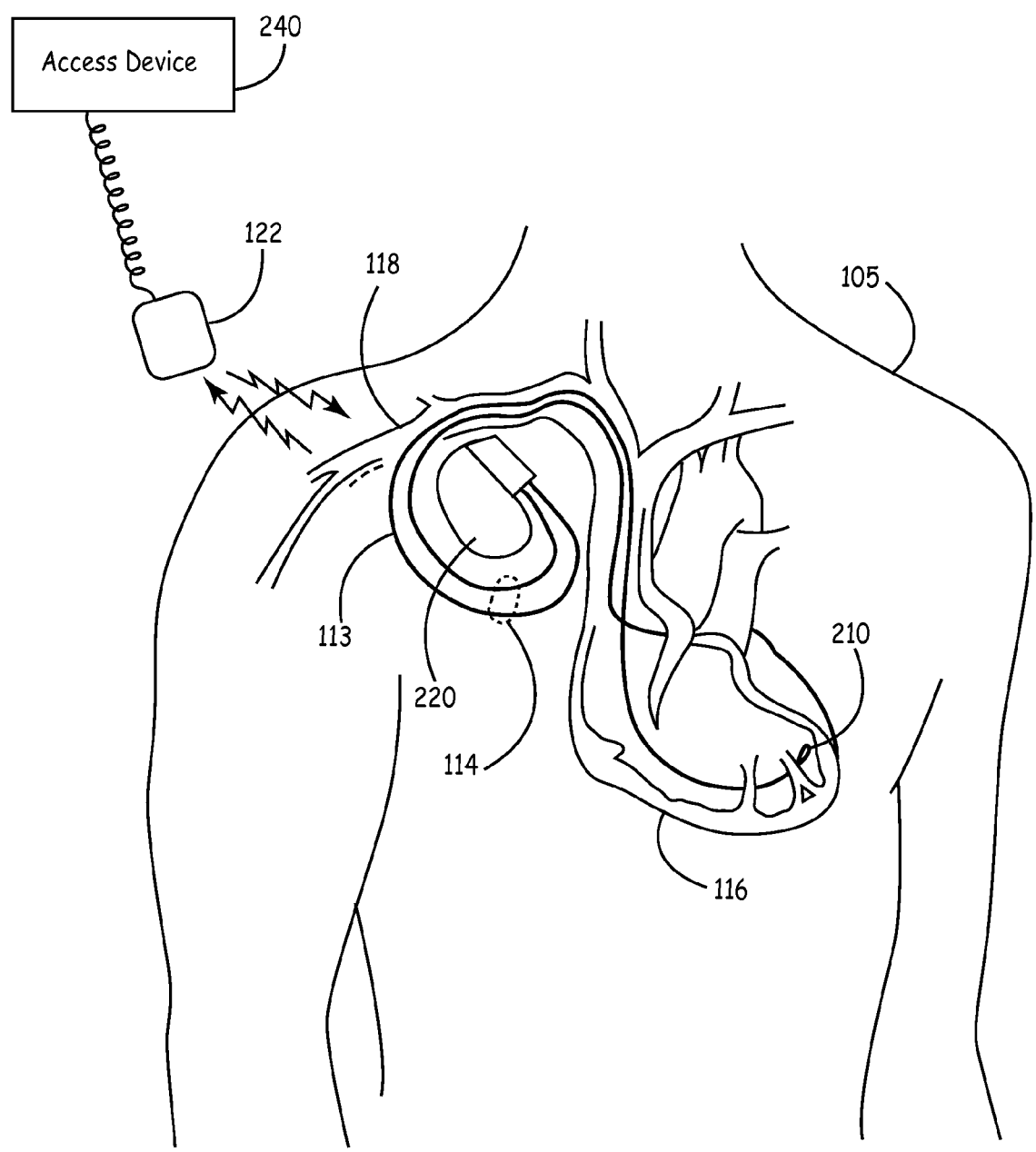
FIG. 1 is a simplified diagram of an implementation of an implantable medical device, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving the operation of implantable medical devices (e.g., pacemakers, cardio defibrillators, and the like). The operation of an implantable medical device includes collecting, storing, and analyzing physiological data relating to a patient, and/or delivering therapy (e.g., cardiac therapy) to a portion of a patient's body. Often, these tasks are performed by an implantable medical system, which includes an implantable medical device. Based upon the analysis performed by the implantable medical system, one or more therapies may be delivered to a particular portion of a patient's body. One example of such a therapy is a cardiac therapy, which is delivered to a patient's heart.

Embodiments of the present invention may be utilized to detect and monitor the common symptoms and conditions related to patients with Obstructive Sleep Apnea (OSA). It should be appreciated that the present invention may be included in an implantable device capable of collecting data other than data used to diagnose or monitor OSA. The data may be collected by sensors in the implantable device and may be used by doctors and other sleep experts to judge the severity of apneas and to determine the efficacy of apnea therapy, without the use of nocturnal polysomnography.

Turning now to FIG. 1, one embodiment of implementing an implantable medical device into a human body is illustrated. A sensor device 210 (e.g., devices attached to leads 114) placed upon the heart 116 of the human body 105 is used to acquire and process physiological data. In one embodiment, the sensor device 210 may also be a therapy delivery device (described in greater detail below). An implantable medical device 220 collects and processes a plurality of data acquired from the human body 105. In one embodiment, the implantable medical device 220 may be a cardiac pacemaker or an implantable cardiovertor defibrillator ("ICD"). The data acquired by the implantable medical device 220 can be monitored by an external system, such as the access device 240 comprising a programming head 122, which remotely communicates with the implantable medical device 220. The programming head 122 is utilized in accordance with medical device programming systems known to those skilled in the art having the benefit of the present disclosure, for facilitating two-way communication between the implantable medical device 220 and the access device 240.

In one embodiment, a plurality of access devices 240 can be employed to collect a plurality of data, including OSA data, processed by the implantable medical device 220 in accordance with embodiments of the present invention. The implantable medical device 220 is housed within a hermetically sealed, biologically inert outer canister or housing 113, which may itself be conductive so as to serve as an electrode in the implantable medical device 220 pacing/sensing circuit. One or more sensors/leads, collectively identified with reference numeral 114 in FIG. 1, are electrically coupled to the implantable medical device 220 and extended into the patient's heart 116 via a vein 118. Disposed generally near a distal end of the leads 114 are one or more exposed conductive electrodes (i.e., sensor device 210) for receiving electrical cardiac signals or delivering electrical pacing stimuli to the heart 116. The leads 114 may be implanted with their distal end situated in either the atrium or ventricle of the heart 116. In an alternative embodiment, the sensor device 210, or the leads 114 associated with the sensor device 210, may be situated in a blood vessel on the heart 116, such as a vein 118.

Figure 2:
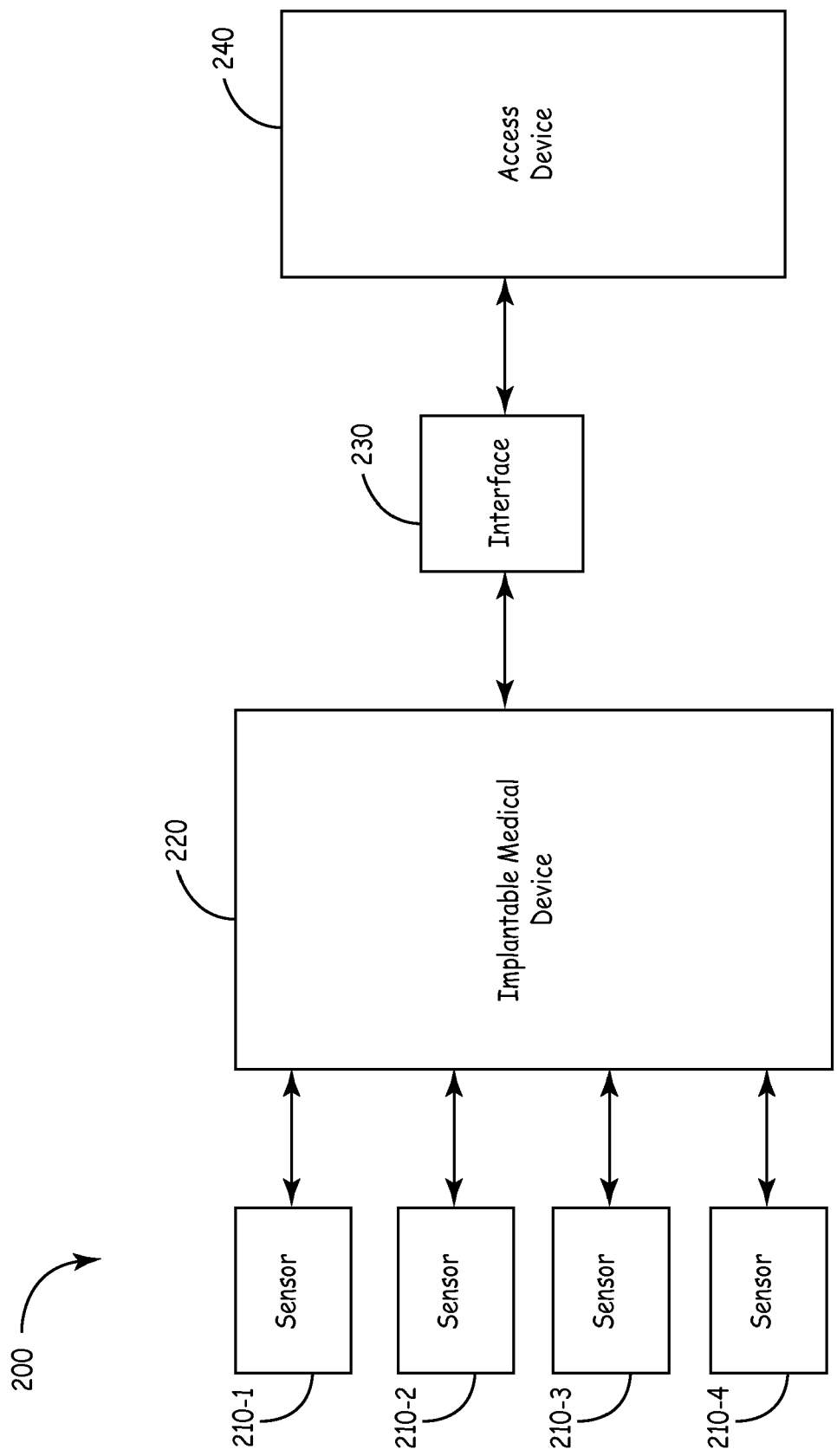
FIG. 2 illustrates a simplified block diagram representation of an implantable medical system in accordance with one illustrative embodiment of the present invention.

Turning now to FIG. 2, a system 200, in accordance with one embodiment of the present invention, is illustrated. The system 200 comprises a plurality of sensor devices, collectively identified with reference numeral 210 in FIG. 2, an implantable medical device 220, an access device 240, and an interface 230 that provides a communication link between the implantable medical device 220 and the access device 240. Embodiments of the present invention provide a plurality of physiological data from the sensor devices 210, which are then processed and stored in the implantable medical device 220. In one embodiment, the sensor devices 210 may collect data that is used to detect and monitor OSA in a patient.

As mentioned, based upon physiological data and other factors, the implantable medical device 220 may deliver a therapy to a portion of the patient's body, via the sensor devices 210. The access device 240 can then be used to monitor and analyze the organized data from the implantable medical device 220 via the interface 230 and view results from delivered therapy. The access device 240 can be used to monitor the efficiency of the therapy delivered by the implantable medical device 220. The access device 240 can be used to determine, based upon data stored by the implantable medical device 220, whether a therapy delivered was of proper energy intensity.

Figure 3:
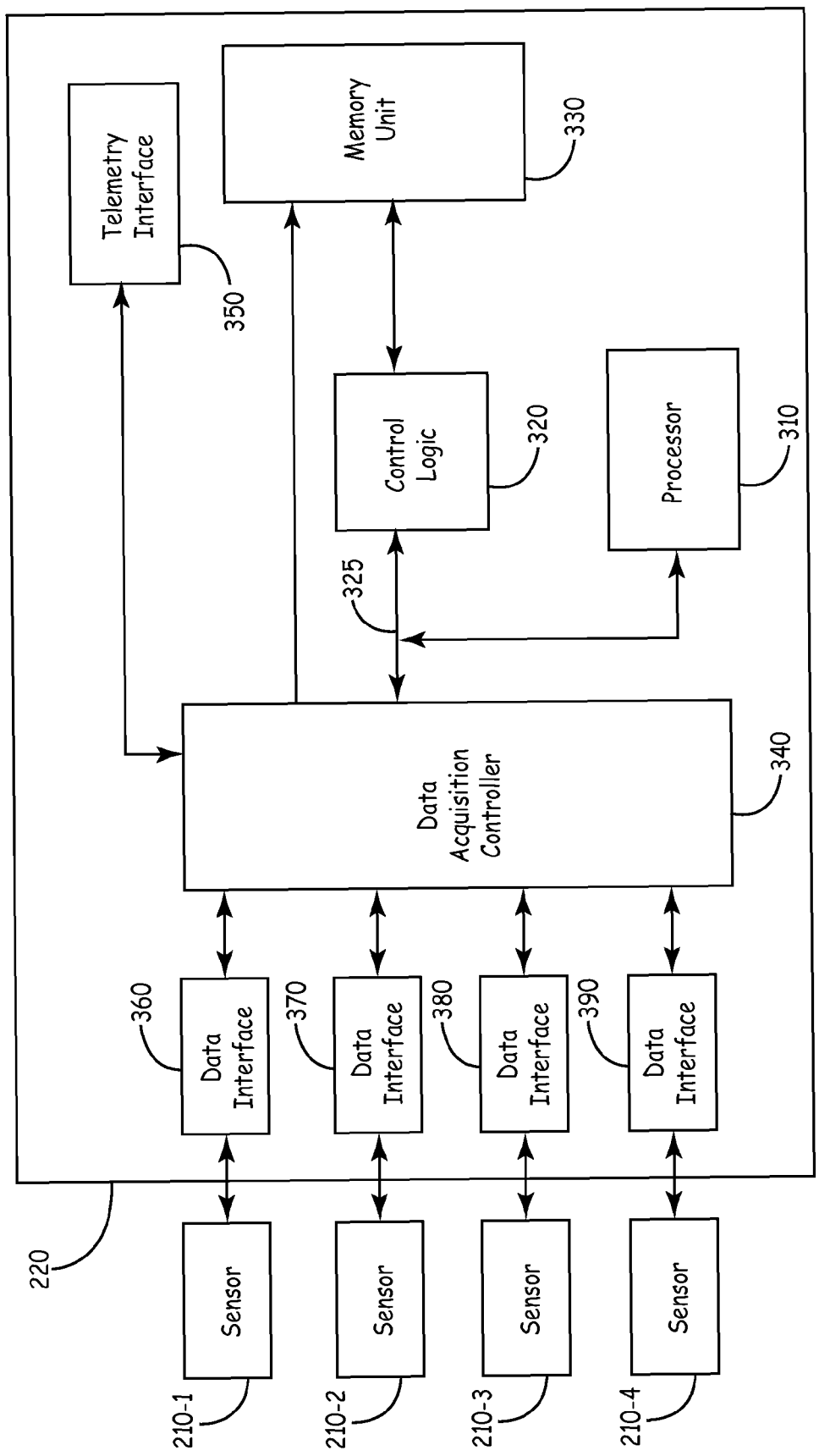
FIG. 3 illustrates a more detailed block diagram representation of the implantable medical device of FIGS. 1 and 2, in accordance with one illustrative embodiment of the present invention.

Turning now to FIG. 3, a more detailed block diagram depiction of one embodiment of the implantable medical device 220 is illustrated. The implantable medical device 220 comprises a processor 310, a control logic 320, a memory unit 330, a data acquisition controller 340, a telemetry interface 350, and a plurality of data interfaces 360, 370, 380, 390. The plurality of sensor devices 210 of FIG. 2 provides various physiological data to the implantable medical device 220. The processor 310 controls the operation of the implantable medical device 220. The processor 310 utilizes the control logic 320 to perform a plurality of operations, including memory access and storage operations. The processor 310 communicates with the control logic 320 and the data acquisition controller 340 via a bus line 325. The control logic 320 sends control signals to the memory unit 330 for controlling and installing the memory unit 330, and to the data acquisition controller 340, which controls the acquisition of physiological data and drives output signals to the telemetry interface 350.

The telemetry interface 350 can facilitate real-time access of physiological data acquired by the data acquisition controller 340. Therefore, a physician can view physiological data on a real time basis by accessing the data acquisition controller 340, via the telemetry interface 350. The data acquisition controller 340 can prompt the data interfaces 360, 370, 380, 390 to retrieve physiological data from the sensor device 210, process such data, and deliver physiological data to the data acquisition controller 340. The data interfaces 360, 370, 380, 390 can perform a number of analog-to-digital conversions and time-interval conversions, known to those skilled in the art, upon the acquired physiological data. The data interfaces 360, 370, 380, 390 can acquire, condition, and process physiological data and forward them to the data acquisition controller 340.

It should be appreciated that, in an alternate embodiment, the functionality of the data interfaces 360, 370, 380, 390 may be combined with the sensor devices 210, such that information gathered by the sensor devices 210 may be readily utilized by the implantable medical device 220 without further processing by another device or interface. It should also be appreciated that, although the sensor devices 210 are separated from the implantable medical device 220 for illustrative purposes in FIGS. 2 and 3, the implantable medical device 220 may further comprise the sensor devices 210.

Turning now to FIG. 4, one embodiment of the sensor device 210 and the implantable medical device 220 of FIGS. 1, 2 and 3, in accordance with the present invention, is shown. In the illustrated embodiment of FIG. 4, four sensors are shown. However, it should be appreciated that the implantable medical device 220 may comprise of more or less sensors than the illustrated embodiment of FIG. 4, such that OSA may be properly diagnosed on a patient. It should also be appreciated that the functionality of each sensor described below may be combined into one or more sensors, such that OSA may be properly diagnosed on a patient.

The implantable medical device 220 comprises four sensors, which individually and in combination may be used to detect OSA in a patient. An intracardiac impedance sensor 210-1 measures impedance between an intracardiac atrial electrode and an intracardiac ventricular electrode. An intrathoracic impedance sensor 210-2 measures impedance across the thorax. In one embodiment, the intrathoracic impedance sensor 210-2 may include pacemaker sensors, which measure impedance between a pacemaker and an intracardiac electrode. The impedance between the pacemaker and the intracardiac electrode may be used to estimate in minute ventilation ("MV"). A movement sensor 210-3 detects movement in a patient during sleep. The movement sensor 210-3, in one embodiment, may be a piezo crystal or an accelerometer. An electrical sensor 210-4 detects cardiac depolarizations.

Using the four sensors 210-1, 210-2, 210-3, 210-4, a plurality of information can be gathered to properly diagnosis OSA on a patient. The information gathered by the sensors 210-1, 210-2, 210-3, and 210-4 is processed by an intracardiac data interface 360, an intrathoracic impedance data interface 370, a movement data interface 380, and an electrical data interface 390, respectively, before the information is forwarded to the data acquisition controller 340. Although sensors can be used individually to diagnose OSA, combinations of two or more sensors may form a basis for diagnosis of OSA. For example, a large decrease in impedance between atrial and ventricular electrodes (i.e., a decrease in the intracardiac impedance sensor 210-1) occurring when a patient is not exercising (i.e., a low reading from the movement sensor 210-3) may be a factor towards diagnosis of OSA. As a patient attempts to breathe while his airway is obstructed, negative intrathoracic pressure may increase, which overfills the right side of the heart. This overfilling of the right side of the heart increases the diameter of the atrium and the ventricle. Although the volume of the heart does not change, the shape of the heart becomes shorter and wider. As a result, a drop in atrial-to-ventricular impedance may be observed during OSA because the wider blood pool will cause a reduced impedance. The wider blood pool may also be a result vigorous exercise from the patient. Therefore, the intracardiac impedance sensor 210-1 may be read in conjunction with the movement sensor 210-3. In one embodiment, a low reading from the movement sensor 210-3 indicates the patient is not exercising or in some other physical activity. A decrease in the intracardiac impedance sensor 210-1 and a low reading from the movement sensor 210-3 indicates a possibility that the patient has OSA.

Another possible indication that a patient has OSA may be provided by the intrathoracic impedance sensor 210-2. In one embodiment, the intrathoracic impedance sensor 210-2 may measure impedance between an implantable device housing, such as a can electrode, and an endocardial electrode, such as an atrial electrode or a ventricular electrode. A decrease in intrathoracic impedance during attempted inspiration may be a factor in determining whether a patient has OSA. As a patient attempts to breathe while his airway is obstructed, the circumference of his thorax may expand. As the patient's thorax expands, the diaphragm pushes the heart and lungs upward. As the lungs are pushed upward, the lungs do not change volume, but instead become shorter and wider. The shorter and wider shape of the lungs may reduce intrathoracic impedance. In addition, as a patient attempts to breathe while his airway is obstructed, negative intrathoracic pressure may increase, which overfills the right side of the heart. As the right side of the heart overflows, a wider blood pathway forms, thereby reducing intrathoracic impedance. Furthermore, upward movement of the diaphragm pushes the heart closer to the implantable medical device 220, thereby reducing impedance. A decrease in the intrathoracic impedance sensor 210-2 indicates the possibility that the patient has OSA.

Another possible indication that a patient has OSA comes from a rapid increase in impedance minute ventilation ("MV") followed by a slower decrease in impedance MV. A person who does not have sleep apnea breathes normally during rest. A patient who has OSA usually cannot breathe normally during rest because of an obstruction in the airway. While the patient's heart is attempting to pump blood into the lungs, the obstruction is preventing the patient from breathing. As a result, the patient's heart begins to pump faster to compensate for the lack of blood flow. After an arousal event, the patient begins to breathe again, but because the heart was pumping fast before the arousal event, the patient goes through a hyperpneic phase, which is a period of abnormally rapid or deep breathing. Studies have shown that during the hyperpneic phase there may be an immediate rise in MV followed by a more gradual drop in MV over a period of time.

An arousal event each time an obstruction is relieved may cause brief periods of movement detectable by the movement sensor. As mentioned, in one embodiment, the movement sensor may be a piezo crystal or an accelerometer. During the hyperpneic phase following the release of an obstruction, there is usually a brief arousal which can cause body movement detectable by movement sensors. A brief period of movement during sleep coinciding with the dramatic increase in respiration (i.e., a rapid increase in impedance MV followed by a slower decrease in impedance MV), as described above, may indicate the patient has OSA. An immediate rise in MV followed by a more gradual drop in MV, coupled with a brief of movement of sleep, indicates the possibility that the patient has OSA.

Yet another possible indication that a patient has OSA may be provided by the electrical sensor 210-4. OSA can cause bradycardia during an obstruction. Bradycardia is an abnormally slow or unsteady heart rhythm (usually less than 60 beats per minute) that causes symptoms such as dizziness, fainting, fatigue, and shortness of breath. Release of the obstruction is generally accompanied by sinus tachycardia and possibly increased atrial-ventricular conduction. Sinus tachycardia is a fast heartbeat (usually more than 150 beats per minute) because of rapid firing of the sinoatrial (i.e., sinus) node. Both sinus tachycardia and increased atrial-ventricular conduction can be detected by intracardiac electrodes and electrical sensing amplifiers or by subcutaneous electrodes and electrical sensing amplifiers.

Referring back to FIG. 3, as the sensors 210-1, 210-2, 210-3, 210-4 collect data, the data interfaces 360, 370, 380, 390 process the data, in accordance with conventional practice, and forwards the data to the data acquisition controller 340. The processor 310 then utilizes the control logic 320 to provide the data from the data acquisition controller to the memory unit 330. In addition, a doctor or another qualified sleep professional may use the telemetry interface 350 to facilitate real-time access to the data on the data acquisition controller. The doctor or another qualified sleep specialist may analyze the collected data to determine whether the patient has OSA.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of detecting and monitoring obstructive sleep apnea, comprising:
   measuring impedance minute ventilation to detect a change in the impedance minute ventilation corresponding to a period of hyperpneic respiration, wherein the change includes an increase in impedance minute ventilation followed by a decrease in impedance minute ventilation;
   detecting an increasing amount of movement of a patient during the period of hyperpneic respiration; and
   determining the presence of obstructive sleep apnea responsive to the change in the impedance minute ventilation coinciding with the increasing movement of the patient.

2. A method of claim 1, wherein measuring impedance minute ventilation further comprises detecting a rapid change in the increase in impedance minute ventilation followed by a gradual change in the decrease in impedance minute ventilation.

3. A method of claim 1, wherein measuring the increasing amount of movement of the patient further comprises detecting an amount of movement of the patient from a state corresponding to a state of physical inactivity of the patient.

4. A medical device for detecting and monitoring obstructive sleep apnea, comprising:
   means for measuring impedance minute ventilation to detect a change in the impedance minute ventilation corresponding to a period of hyperpneic respiration, wherein the change includes an increase in impedance minute ventilation followed by a decrease in impedance minute ventilation;
   means for detecting an increasing amount of movement of a patient during the period of hyperpneic respiration; and means for determining the presence of obstructive sleep apnea responsive to the change in the impedance minute ventilation coinciding with the increasing movement of the patient.

5. The method of claim 1, further comprising:

correlating a decrease in intrathoracic impedance during an attempted inspiration of the patient with the presence of obstructive sleep apnea.

6. The method of claim 1, wherein the impedance minute ventilation is measured between an electrode in an atrium of a heart and an electrode in a ventricle of a heart.

7. The method of claim 1, wherein the impedance minute ventilation is measured between an implantable device housing and an endocardial electrode.

8. The method of claim 5, further comprising detecting an arousal of a patient from sleep coinciding with the occurrence of the attempted inspiration.

9. The method of claim 8, further comprising determining an occurrence of obstructive sleep apnea in response to detecting the occurrence of the attempted inspiration of the patient coinciding with detection of arousal of the patient from sleep.

* * * * *